United States Patent [19]

Teirstein

[11] Patent Number: 5,472,425
[45] Date of Patent: Dec. 5, 1995

[54] RAPID EXCHANGE CATHETER

[76] Inventor: Paul S. Teirstein, 402 Coast Blvd., South, La Jolla, Calif. 92037

[21] Appl. No.: 231,423

[22] Filed: Apr. 22, 1994

Related U.S. Application Data

[63] Continuation-in-part of Ser. No. 197,970, Feb. 17, 1994, which is a continuation of Ser. No. 92,332, Jul. 15, 1993, Pat. No. 5,336,184.

[51] Int. Cl.⁶ .................................................. A61M 29/00
[52] U.S. Cl. ................................ 604/102; 604/96; 604/53
[58] Field of Search ............................. 604/96–103, 53, 604/158, 160, 164; 606/194

[56] References Cited

U.S. PATENT DOCUMENTS

| | | | |
|---|---|---|---|
| 4,748,982 | 6/1988 | Horzewski et al. | 604/102 |
| 4,762,129 | 8/1988 | Bonzel . | |
| 4,771,777 | 9/1988 | Horzewski et al. . | |
| 4,819,751 | 4/1989 | Shimada et al. . | |
| 4,909,781 | 3/1990 | Husted . | |
| 4,944,745 | 7/1990 | Sogard et al. . | |
| 4,983,167 | 1/1991 | Sahota | 604/96 |
| 4,988,356 | 1/1991 | Crittenden et al. | 606/192 |
| 5,040,548 | 8/1991 | Yock . | |
| 5,061,273 | 10/1991 | Yock . | |
| 5,135,535 | 8/1992 | Kramer | 604/102 |
| 5,147,377 | 9/1992 | Sahota . | |
| 5,154,725 | 10/1992 | Leopold . | |
| 5,156,594 | 10/1992 | Keith . | |
| 5,171,222 | 12/1992 | Euteneuer et al. . | |
| 5,180,367 | 1/1993 | Kontos et al. | 604/101 |
| 5,205,822 | 4/1993 | Johnson et al. . | |
| 5,232,445 | 8/1993 | Bonzel . | |
| 5,267,958 | 12/1993 | Buchbinder et al. | 604/96 |
| 5,324,269 | 6/1994 | Miraki | 604/96 |
| 5,336,184 | 8/1994 | Teirstein | 604/102 |
| 5,342,297 | 8/1994 | Jang | 604/96 |
| 5,346,505 | 9/1994 | Leopold | 604/96 |

FOREIGN PATENT DOCUMENTS

WO92/17236  10/1992  WIPO .

Primary Examiner—C. Fred Rosenbaum
Assistant Examiner—Frank Wilkens, III
Attorney, Agent, or Firm—Nydegger & Associates

[57] ABSTRACT

An over-the-wire rapid-exchange catheter having a guidewire channel and a rupturable membrane along one side of the guidewire channel. The catheter is exchanged by withdrawing the catheter from a guiding catheter, while stripping the operative catheter from the guidewire by tearing the guidewire through the rupturable membrane. The guidewire channel provides a sealing surface for a releasable seal on the guiding catheter, avoiding the gripping of the guidewire. A replacement catheter can be threaded onto the guidewire, and the end of the guidewire can puncture the rupturable membrane at a selected location to establish a guidewire channel at the distal end of the catheter.

11 Claims, 3 Drawing Sheets

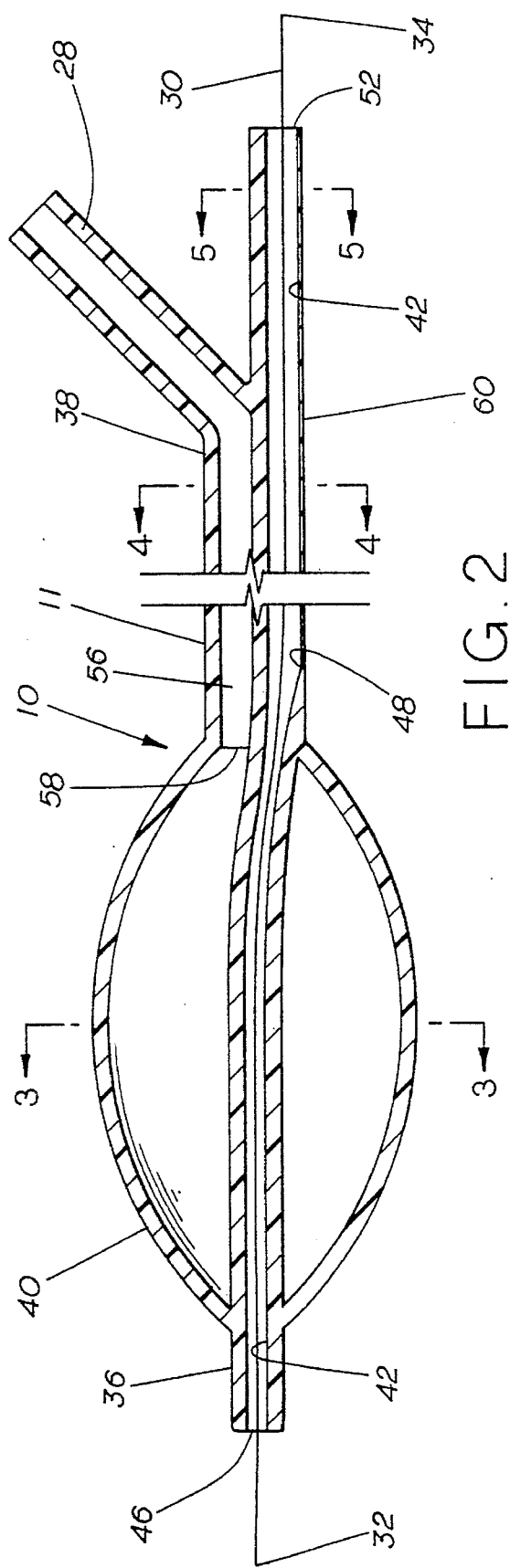

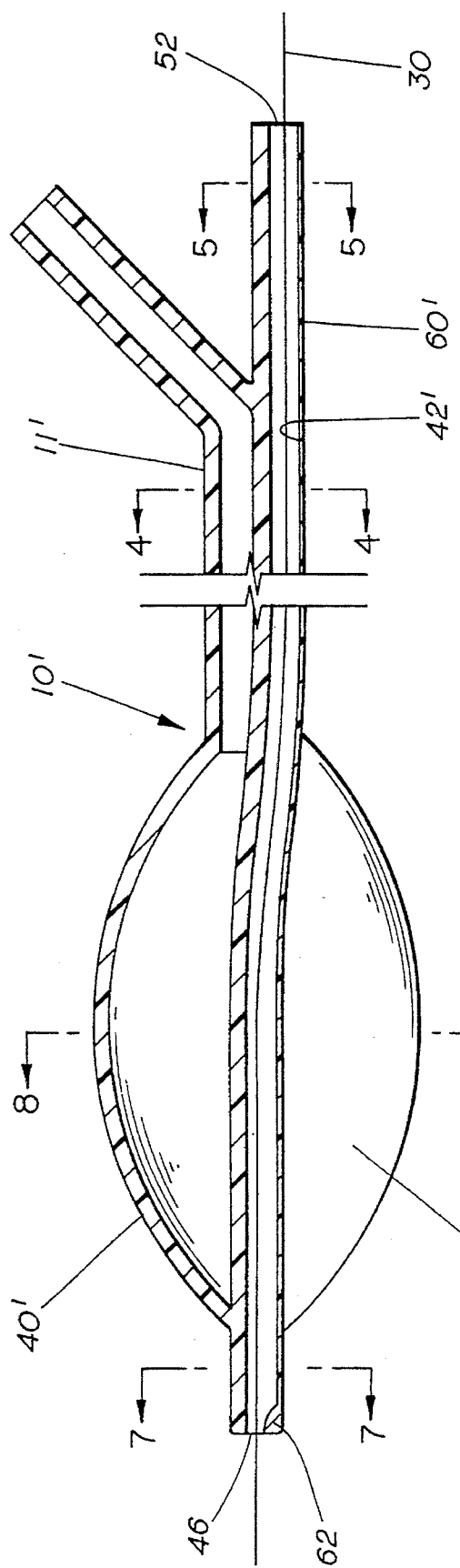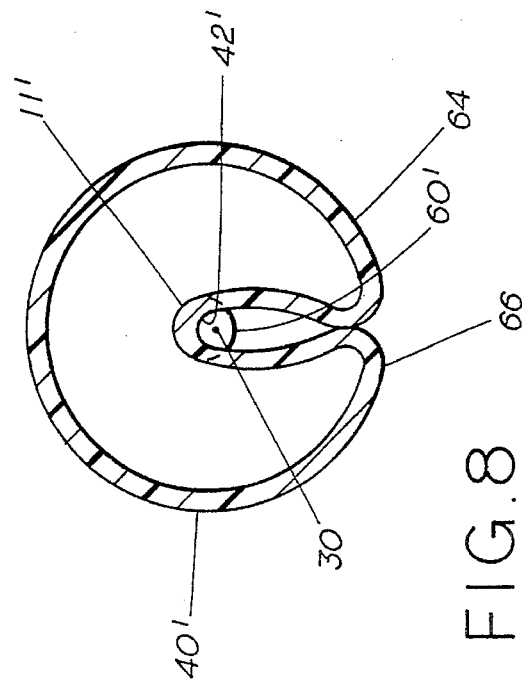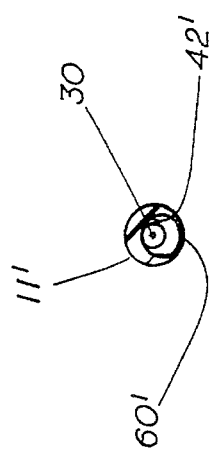
FIG. 6
FIG. 8
FIG. 7

RAPID EXCHANGE CATHETER

RELATED APPLICATION

This application is a continuation-in-part of U.S. patent application Ser. No. 197,970, filed Feb. 17, 1994, now pending, which is a continuation of U.S. patent application Ser. No. 092,332, filed Jul. 15, 1993 now U.S. Pat. No. 5,336,184.

FIELD OF INVENTION

The present invention is in the field of catheters which are inserted into body passageways of patients for various diagnostic and therapeutic treatment. Specifically, this invention pertains to a diagnostic or therapeutic catheter which can be inserted over a guidewire, followed by removal and replacement of the diagnostic or therapeutic catheter, over the same guidewire. Such catheters are commonly referred to as over-the-wire and rapid-exchange catheters.

BACKGROUND OF THE INVENTION

Over-the-wire and rapid-exchange catheters are adaptable for various applications involving various body passageways or cavities, one of which is an intravascular procedure called percutaneous transluminal coronary angioplasty (PTCA) for dilatation of a coronary stenosis. During the performance of the PTCA procedure, it is often necessary to remove the operative catheter, whether diagnostic or therapeutic in nature, and replace it with another operative catheter.

In the performance of a typical PTCA procedure, a guiding catheter is percutaneously introduced into the cardiovascular system of the patient. This guiding catheter typically has a distal tip which is shaped to enhance its ability to be advanced to the vicinity of the selected treatment area. The guiding catheter can be twisted or rotated to orient the shaped distal tip to follow the vascular passageways as desired. The distal tip of the guiding catheter is advanced through the cardiovascular system to the aorta, near the ostium, or mouth, of the coronary artery to be inspected or treated. At this point, the shaped distal tip of the guiding catheter is oriented into the coronary ostium.

An operative catheter is then inserted into the guiding catheter and advanced to the treatment area. The guiding catheter will typically incorporate a releasable seal near its proximal end, to seal the guiding catheter around the operative catheter and prevent back leakage of contrast dye or other fluids. The seal is typically an O-ring which can have its internal opening tightened around the operative catheter. The tightness of the seal is selectively adjusted by the physician during the procedure as required to allow movement of the catheter or guidewire, and to maintain a fluid tight seal. The operative catheter can have various operative means on its distal end, for diagnostic or therapeutic purposes. Other procedures could utilize a laser source or an image guide, or other means as required, but in the case of the PTCA procedure, the operative means is an inflatable angioplasty balloon. In the typical over-the-wire procedure, the operative catheter has a guidewire running through an inner guidewire channel in the catheter body. This guidewire channel is usually separate from the operative or communicative channel which operates the operative means, such as by inflating the angioplasty balloon in the PTCA procedure.

The guidewire runs from the proximal end of the operative catheter, through the guidewire channel, and out the distal end of the catheter body. The distal tip of the guidewire is normally shaped to facilitate its advancement into the coronary artery to be treated. The distal tip of the guidewire is advanced out the distal end of the operative catheter, past the ostium of the coronary artery, along the selected coronary artery to the treatment point. The guidewire can be twisted or rotated as required to orient the shaped distal tip of the guidewire to facilitate passage through the artery. The operative catheter can be sequentially moved along with the guidewire, or the guidewire can be advanced alone, to be followed by the operative catheter. Many physicians prefer to sequentially advance the operative catheter to assist in guiding the guidewire tip. For example, when two or more curves in the vascular passageway are encountered, it is often helpful to advance the guidewire through the first curve and then bring the operative catheter over the guidewire into the first curve. Then, the guidewire is advanced through the second curve, assisted by the support of the operative catheter. This calls for smooth movement of the operative catheter and guidewire, without interference from any unnecessary drag from the releasable seal, to allow the physician to feel the progress of the guidewire and catheter.

Eventually, in the PTCA procedure, the distal tip of the guidewire is advanced through the stenosis in the coronary artery. The operative dilatation catheter is then advanced over the guidewire until the balloon on the distal end of the operative catheter is positioned across the stenosis. The balloon is then inflated to dilate the stenosed area of the artery, deflated, and withdrawn to allow the resumption of blood flow. It is often necessary to withdraw the operative catheter and replace it with a second operative catheter to perform a different procedure, or to more effectively perform the procedure at hand. An example of the need for such an exchange can be to replace the balloon with a balloon of a different size.

Catheters have been devised which will allow the removal of the first operative catheter while holding the guidewire in place, followed by the insertion of a second operative catheter over the original guidewire. During this procedure, called a rapid exchange, it is still necessary to feel the advance of the operative catheter through the vascular passageways. It is also necessary to hold the guidewire in place, to avoid the time and risk involved in inserting a second guidewire, and to prevent the guidewire from partially withdrawing with the catheter. Most rapid exchange catheters have simply used a guidewire channel located near the distal end of the catheter body, through which the guidewire is threaded. From this distal guidewire channel, the guidewire typically simply passes alongside the catheter body to the proximal end of the catheter. This allows the physician to hold the guidewire in place while withdrawing the operative catheter until the distal guidewire channel has exited the guiding catheter. The physician can then grasp the guidewire beyond the distal end of the operative catheter and fully withdraw the operative catheter over the proximal end of the guidewire. The proximal end of the guidewire is then inserted through the distal guidewire channel on the replacement operative catheter, and the catheter is inserted to the treatment area over the guidewire.

The principal problem with such rapid exchange catheters is that the guidewire passes alongside the catheter body over most of its length. This means that the releasable seal in the guiding catheter must seal against the guidewire by pressing the guidewire against the outer surface of the operative catheter. This creates a significant drag on the guidewire, which interferes with the physician's tactile feedback during initial insertion of the guidewire from the coronary ostium to the stenosis. This condition is undesirable, especially at this particular juncture in the PTCA procedure, when the physician particularly needs the maximum possible tactile feedback.

In addition, it is difficult to coordinate the advancement of the catheter and separate guidewire through the guiding catheter, because they must be handled as two separate filaments. One reason for this is that when the releasable seal is tightened against the catheter and guidewire, such as during dye injection, the guidewire exits the guiding catheter at an extreme angle relative to the operative catheter, which feels awkward to the physician.

A second problem with known rapid exchange catheters is that the length of the distal guidewire channel is set, and the physician has no choice as to where the guidewire exits the guidewire channel. This can lead to the distal guidewire channel being too short, for instance. The excessively short guidewire channel can cause a problem in a particular patient when, during withdrawal of the catheter, a segment of the wire is pulled proximally by the guidewire channel, resulting in the creation of a loop or prolapse of wire, rather than the smooth tracking of the catheter along the wire. In addition, if the artery has any loose flaps of tissue, these flaps can become snagged during removal of the catheter from the vessel, by the vee-shape formed between the catheter and guidewire. Further, if the guidewire channel is too short, trackability of the catheter during insertion is reduced. To remedy these problems, it can be helpful to be able to space the guidewire exit port farther from the distal end of the catheter, when a replacement catheter is installed.

On the other hand, the distal guidewire channel can be too long. A longer channel can create more resistance to insertion of a replacement catheter. Also, upon removal of a catheter from the wire, as the distal guidewire channel begins to exit the guiding catheter, the physician must release his grip on the guidewire and move his grip farther away from the guiding catheter, then withdraw the operative catheter until the guidewire channel again contacts his grip on the wire, and then continue repeating the process until the guidewire channel completely exits the guiding catheter. If the distal guidewire channel is long, this process can take additional time and increase the possibility of unintentionally withdrawing the wire a short distance. It can be seen that the optimum length of distal guidewire channel can vary from procedure to procedure.

Therefore, it is an object of the present invention to provide a catheter which will allow the physician increased tactile feedback during advancement of the guidewire from the distal mouth of the guiding catheter through the stenosis and during advancement of the operative catheter over the guidewire. It is a further object of the present invention to provide a catheter in which the guidewire does not contact the releasable seal in the guiding catheter, and which presents a smooth sealing surface to the releasable seal. It is a still further object of the present invention to provide a catheter which allows the physician to easily determine the placement of the guidewire exit port during installation of the replacement catheter. Further yet, it is an object of the present invention to provide a catheter which allows the physician to strip the wire from the guidewire channel to a desired point, during removal of the catheter, and to reuse the catheter later during the procedure. Finally, it is an object of the present invention to provide a catheter which will allow the physician to easily and completely strip the guidewire from the catheter during removal of the catheter from the patient, without releasing the grip on the wire, if desired.

SUMMARY OF THE INVENTION

The present invention provides an over-the-wire rapid-exchange catheter which has an integral guidewire channel running the full length of the catheter body. The guidewire channel is a lumen passing longitudinally through the catheter body, sized to allow the free passage of a guidewire. The guidewire channel has two original ports through which the guidewire enters and exits the guidewire channel. The guidewire channel also has a rupturable membrane along one side of the channel, constituting a very thin wall of the catheter body. The rupturable membrane is thin enough to allow the guidewire to easily be torn through the membrane, if desired by the physician, as the catheter is removed from the guiding catheter. Prior to tearing, the rupturable membrane provides a fluid barrier against leakage of fluid out of the blood vessel or guiding catheter and past the releasable seal. In one embodiment, the rupturable membrane extends along one side of the guidewire channel from the proximal end of the catheter body to a point just proximally from the balloon. In another embodiment, the rupturable membrane extends all the way from the proximal end of the catheter body to the distal end, beyond the balloon. The passage of the guidewire through the guidewire channel will be described by the use of the terms "enter" and "exit" as they would apply during threading of the proximal end of the guidewire through the guidewire channel from the distal end of the catheter body toward the proximal end of the catheter body.

The operative catheter of the present invention has a flexible elongated catheter body. It is to be understood that the principles of the invention also could apply to a rigid catheter using an internal guide means or to a catheter of any length. A guidewire channel is formed into the catheter body from the distal end of the catheter body, along the catheter body to the proximal end. The distal end of the guidewire channel contains a guidewire entry port which is located at the extreme distal tip of the operative catheter. The proximal end of the guidewire channel contains a guidewire exit port through which the guidewire exits the guidewire channel.

The exact configuration of the distal end of the guidewire channel can be designed, in one embodiment, as is well known in the art according to the type of operative means mounted on the distal end of the operative catheter. Where the operative means is an angioplasty balloon, the guidewire channel can pass through or alongside the balloon to the distal end of the catheter, and the guidewire extends out the extreme distal end of the guidewire channel. In one embodiment of the present invention, the rupturable membrane extends from a point proximal to the balloon to the proximal end of the catheter. The guidewire can be torn through the membrane while withdrawing the operative catheter from the guiding catheter. This allows the catheter to be withdrawn over the in-place guidewire until the balloon begins to exit the guiding catheter, followed by grasping of the guidewire beyond the balloon to allow complete removal of the catheter from the proximal end of the guidewire. In another embodiment, the membrane extends beyond the balloon, and the wire can be stripped completely from the catheter, without releasing the grip on the wire.

The extension of the guidewire channel for the full length of the catheter is designed to ensure that the releasable seal on the guiding catheter is situated around the guidewire channel during the time when the guidewire and operative catheter are being advanced out of the distal end of the guiding catheter into the stenosed region of the artery. As explained earlier, the guiding catheter is inserted until its distal end is at the ostium of the artery. Subsequently, the operative catheter and its threaded guidewire are advanced through the guiding catheter until the distal end of the operative catheter is just short of the distal end of the guiding catheter. A reference mark on the catheter body aligns with the proximal end of the guiding catheter to demonstrate when the operative catheter has been inserted to this depth. This reference mark is located longitudinally on the catheter body at a position which incorporates the guidewire channel, so that the guidewire does not contact the releasable seal at the proximal end of the guiding catheter.

This ensures that, once the operative catheter has been inserted nearly to the distal end of the guiding catheter at the ostium of the artery, the further stepwise sequential advancement of the guidewire and the operative catheter to enter the artery, advance through the stenosis, and dilate the stenosis will take place without the releasable seal contacting the guidewire. Therefore, less pressure on the seal will be required, and increased tactile feedback will be provided to the physician. In addition, the guidewire will exit the catheter body essentially parallel to the catheter body, rather than at an awkward angle. Finally, the tightness of the releasable seal can be set, and advancement of the guidewire can take place without further adjustment.

During replacement of the operative catheter, the guidewire exit port can be chosen by the physician to be near the distal end of the catheter, for instance, to increase speed of insertion. Or, the exit port can be chosen to be farther from the distal end, to inhibit accidental slip-out of the guidewire.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 2 is a longitudinal sectional view of the operative catheter shown in FIG. 1;

FIG. 3 is a transverse sectional view of the operative catheter shown in FIG. 2, taken at line 3—3;

FIG. 4 is a transverse sectional view of the operative catheter shown in FIG. 2, taken at line 4—4;

FIG. 5 is a transverse sectional view of the operative catheter shown in FIG. 2, taken at line 5—5; and FIG. 6 is a longitudinal sectional view of an alternate embodiment of the operative catheter of the present invention, showing the rupturable membrane extending beyond the balloon;

FIG. 7 is a transverse sectional view of the operative catheter shown in FIG. 6, taken at line 7—7;

FIG. 8 is a transverse sectional view of the operative catheter shown in FIG. 6, taken at line 8—8.

DESCRIPTION OF PREFERRED EMBODIMENTS

Figure 1:
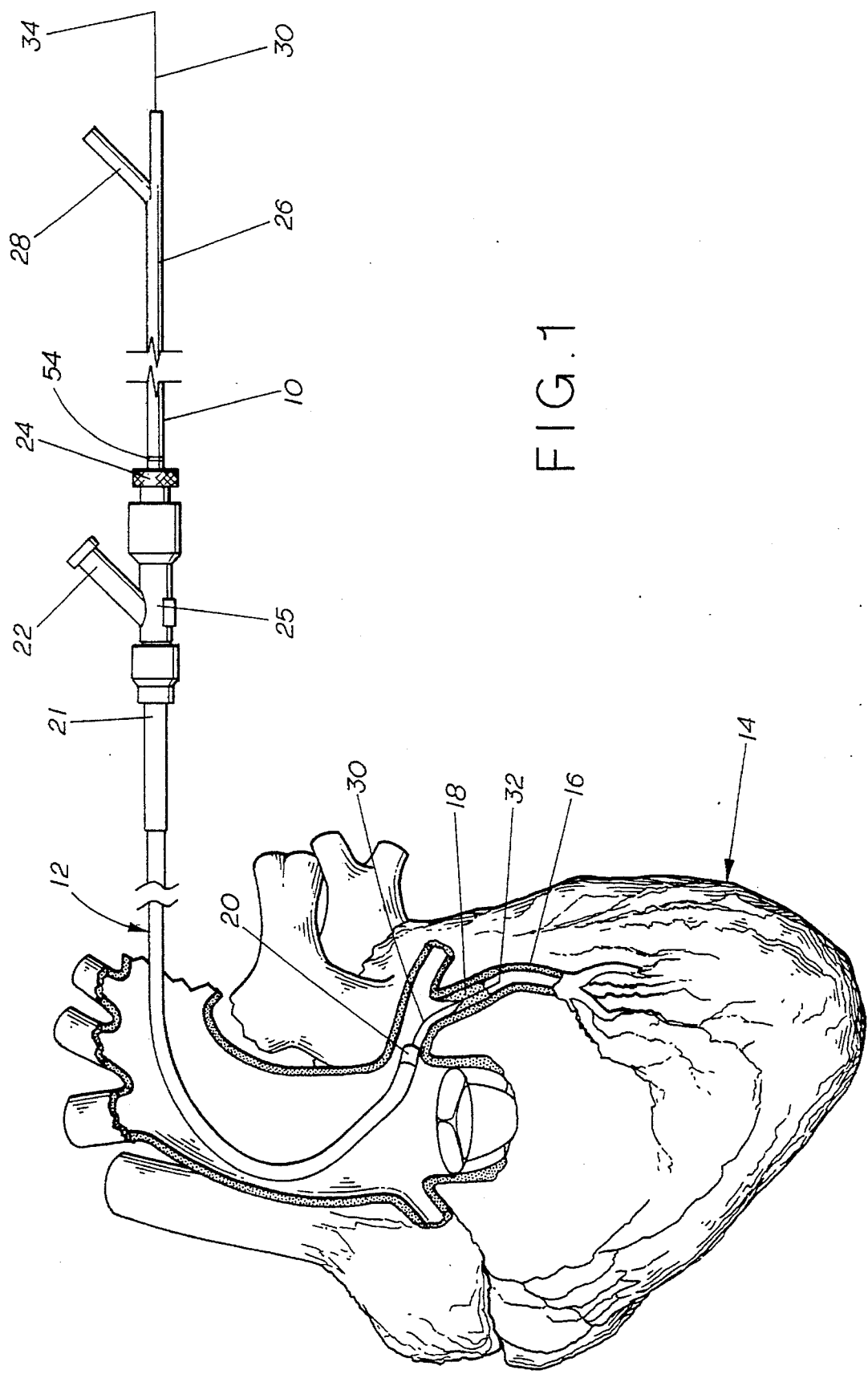
FIG. 1 is a schematic view of the operative catheter of the present invention in use.

As seen in FIG. 1, when in use, the operative catheter 10 is inserted through guiding catheter 12, which has been inserted, through the arteries, to the heart 14 of a patient. Heart 14 has a coronary artery 16 which is partially or completely occluded by stenosis 18. Distal end 20 of guiding catheter 12 has been positioned at the ostium of coronary artery 16, and guidewire 30 has been advanced toward stenosis 18. Distal end 32 of guidewire 30 is shown as having passed through stenosis 18 prior to advancement of operative catheter 10 out of guiding catheter 12, but in many situations, operative catheter 10 would be sequentially advanced in a step-wise fashion along with guidewire 30. It is also possible to use the catheter of the present invention without a guiding catheter.

Proximal end 21 of guiding catheter 12 is joined to an adaptor 25 which contains releasable seal 24. Releasable seal 24 typically contains an O-ring which can be tightened to seal its internal opening around operative catheter 10 by tightening a nut. Contrast dye injection port 22 projects at an angle from adaptor 25. Adaptor 25 functions essentially as the proximal terminal of guiding catheter 12, and the proximal end of adaptor 25 will be considered, for the purposes of this discussion, to be the proximal end of guiding catheter 12. Guiding catheter 12, adaptor 25, and releasable seal 24 are items well known in the art. In FIG. 1, operative catheter 10 has been inserted into guiding catheter 12, through adaptor 25, until the distal end of operative catheter 10 is near, but just short of distal end 20 of guiding catheter 12.

A length of operative catheter 10 extends proximally from the proximal end of guiding catheter 12, with a Y-shaped fitting 26 formed thereon. Fitting 26 has proximal end 34 of guidewire 30 extending therethrough, and inflation port 28 projects at an angle from fitting 26. Inflation fluid is injected into inflation port 28 to inflate an angioplasty balloon on the distal end of operative catheter 10. Fitting 26 functions essentially as the proximal terminal of operative catheter 10, and the proximal end of fitting 26 will be considered, for the purposes of this discussion, to be the proximal end of operative catheter 10.

As seen in FIG. 2, operative catheter 10 includes flexible elongated catheter body 11 having distal end 36 and proximal end 38. Angioplasty balloon 40 is mounted adjacent to distal end 36. A hollow guidewire channel 42 is formed into catheter body 11 throughout the length thereof. The guidewire channel 42 has a distal guidewire entry port 46 at its extreme distal end, and from there to a point 48 just proximal of balloon 40, the guidewire channel wall has a relatively uniform thickness throughout its circumference, as shown in FIGS. 2 and 3. This thickness is sufficiently thick to resist tearing by any normally encountered lateral forces on the guidewire 30, and to resist puncture by the guidewire 30. From the point 48 to a guidewire exit port 52 at the proximal end, guidewire channel 42 has one side of its wall formed by a very thin membrane 60. Membrane 60 is thick enough to form an effective fluid barrier in the original state, and to resist accidental tearing or puncture by the guidewire 30. On the other hand, it is sufficiently thin that it can be intentionally torn by the physician, by pulling outwardly on the guidewire 30, or it can be intentionally punctured by the end of the guidewire 30 to create a guidewire exit port. While very thin, the membrane 60 is of uniform thickness, to allow the physician to tear or puncture the membrane at any axial or angular location, without having to tear or puncture the guidewire channel wall at a particular location where a weak point might be located. This allows the physician much more flexibility in choosing an exit port location, and it makes the catheter much easier to use. Reference mark 54 is placed on catheter body 11, around guidewire channel 42, between balloon 40 and exit port 52.

Balloon 40 is mounted to catheter body 11 surrounding guidewire channel 42, between entry port 46 and point 48. Guidewire 30 passes through catheter body 11, within guidewire channel 42, then finally exits catheter body 11 at exit port 52. Balloon 40 is inflated via inflation channel 56 and balloon port 58. Inflation channel 56 is parallel to but isolated from guidewire channel 42. FIG. 3 shows the distal section of guidewire channel 42 in relation to balloon 40. FIG. 4 shows the proximal section of guidewire channel 42 in relation to inflation channel 56. FIG. 5 shows the proximal end of the guidewire channel 42. In this embodiment, the proximal section of guidewire channel 42 is formed along the edge of catheter body 11, next to inflation channel 56, and the distal section of guidewire channel 42 is formed substantially coaxially with balloon 40.

FIG. 6 shows an alternate embodiment of the catheter 10' of the present invention which allows the rupturable membrane 60' to pass all the way from the proximal end to the distal end of guidewire channel 42'. A very short section 62, approximately 1 millimeter long, of guidewire channel 42' has a relatively thick wall to resist tearing by guidewire 30. Section 62 can be formed with a slightly reduced wall thickness to allow tearing, but requiring additional force beyond the force required to tear the rupturable membrane 60'. As seen in FIG. 7, the rupturable, relatively thin membrane 60' passes all the way from the proximal end of the catheter body 11' to the thicker walled section 62. In order to allow the rupturable membrane 60' to extend the full length of the catheter body 11', the guidewire channel 42' does not pass through the balloon 40'. Instead, as shown in FIG. 8, the balloon 40' has two lobes 64, 66 which form around the guidewire channel 42' when balloon 40' is inflated. This leaves rupturable membrane 60' exposed to the exterior of balloon 40'. The proximal portion of this alternate embodiment 10' is the same as the first embodiment 10, at lines 4—4 and 5-5, as shown in FIGS. 4 and 5.

OPERATION

Guiding catheter 12 is inserted through vascular passageways to the ostium of coronary artery 16. Operative catheter 10, with guidewire 30 threaded therethrough, is inserted into guiding catheter 12 until reference mark 54 is at the proximal end of guiding catheter 12. This ensures that the distal end of operative catheter 10 is near, but just short of, the distal end of guiding catheter 12. Seal 24 is tightened as required. Guidewire 30 and operative catheter 10 are sequentially advanced in a stepwise fashion across stenosis 18. Dilatation can then be accomplished.

When exchange of the operative catheter is required, guidewire 30 is pulled to the side toward the rupturable membrane 60, to tear through the membrane 60. The tearing or rupturing need not take place at any particular angular location on the membrane 60; therefore the physician need not direct the side of the guidewire 30 toward a particular angular location on the membrane 60 to initiate tearing. The physician also has some flexibility in the angular orientation of the guidewire 30 relative to the catheter 10 during stripping of the catheter 10 from the guidewire 30. Operative catheter 10 is withdrawn while stripping the guidewire 30 through rupturable membrane 60 down the length of the catheter body 11. Guidewire 30 is held in place in the guiding catheter 12 while operative catheter 10 is withdrawn until point 48 at the proximal end of balloon 40 exits the guiding catheter 12. This is the point at which the rupturable membrane 60 stops, so no further stripping of guidewire 30 is possible. Balloon 40 is then withdrawn over guidewire 30 until the distal entry port 46 is withdrawn from the guiding catheter 12. Guidewire 30 is grasped beyond the operative catheter 10, and the catheter 10 is completely removed from the proximal end 34 of guidewire 30.

A replacement operative catheter 10 is threaded onto proximal end 34 of guidewire 30, until the proximal end 34 of guidewire 30 is at a selected point proximally of balloon 40. Catheter 10 is then bent so as to expose rupturable membrane 60 on the outside of the bend, and the proximal end 34 of guidewire 30 is pushed through the rupturable membrane 60. This puncture can take place at any axial or angular location on membrane 60, since membrane 60 has an essentially uniform puncturable wall thickness and does not rely on designated weak spots. This greatly facilitates puncture of the membrane 60 by the physician, without having to direct the end 34 of guidewire 30 at a particular weak spot. Replacement catheter 10 is then advanced to the stenosis 18, in the fashion of a typical rapid exchange catheter, while original guidewire 30 is held in place. The point at which the proximal end 34 of guidewire 30 pierces the rupturable membrane 60 can be selected by the physician according to the needs of the particular application. In some cases, piercing will be done near point 48 adjacent balloon 40, but in others, the guidewire 30 will pierce the rupturable membrane 60 at a point farther proximal of the balloon 40. This latter exit point can be useful if the blood vessel being followed has a series of closely spaced turns, or to avoid another of the aforementioned mishaps, such as avoiding the snagging of any tissue fragments between the catheter body 11 and guidewire 30 during withdrawal.

The alternate embodiment of catheter 10' is used in much the same way as the first embodiment, except that, when removing the original catheter 10', the guidewire 30 can be stripped through the rupturable membrane 60' all the way to the thicker wall section 62 at the distal end 36 of the catheter body 11'. This makes the procedure even easier, because once the stripping of the catheter 10' has been completed, the entire catheter including the balloon 40' has exited the guiding catheter. If desired, the guidewire 30 can then be forcibly pulled through the final section 62. Installation of a replacement catheter 10' is accomplished in the same manner as with catheter 10.

While the particular Improved Rapid Exchange Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An operative catheter, comprising:
   an elongated catheter body having a distal end and a proximal end;
   a branch formed on said catheter body distal from said proximal end;
   an operative means mountable on said catheter body adjacent said distal end of said catheter body, for performing a diagnostic or therapeutic operation on a patient;
   a communicative means extending through said catheter body from said branch on said catheter body to said operative means;
   a guidewire channel formed on said catheter body, said guidewire channel having a distal entry port and a proximal exit port; and a rupturable membrane formed in a wall of said guidewire channel, extending from said proximal end of said catheter body toward said distal end, said membrane being sufficiently thin to be parted by a guidewire at a location selected by the user.

2. An operative catheter as claimed in claim 1, wherein:

said operative means comprises an angioplasty balloon; and said rupturable membrane extends the full length of said catheter body from said proximal end to a location beyond said balloon.

3. An operative catheter as claimed in claim 2, wherein said communicative means comprises a fluid passageway extending longitudinally through said catheter body from said branch of said catheter body to said balloon.

4. A vascular catheter system, comprising:

an elongated guiding catheter having a distal end and a proximal end;

a releasable seal mountable on said guiding catheter adjacent said proximal end of said guiding catheter;

an elongated operative catheter body having a distal end and a proximal end, said operative catheter body being insertable through said guiding catheter to an area to be treated;

a branch formed on said catheter body distal from said proximal end;

an operative means mountable on said operative catheter body adjacent said distal end of said operative catheter body, for performing a diagnostic or therapeutic operation on a patient;

a communicative means extending through said operative catheter body from said branch on said operative catheter body to said operative means;

a guidewire channel formed on said operative catheter body, said guidewire channel having a distal port and a proximal port;

a guidewire passing through said guidewire channel, with a distal end of said guidewire extending distally through said distal port and a proximal end of said guidewire extending proximally through said proximal port; and a rupturable membrane formed in a wall of said guidewire channel, extending from said proximal end of said catheter body toward said distal end, said membrane being sufficiently thin to be parted by said guidewire at a location selected by the user.

5. A vascular catheter system as claimed in claim 4, wherein:

said operative means comprises an angioplasty balloon; and said rupturable membrane extends the full length of said catheter body from said proximal end to a location beyond said balloon.

6. A vascular catheter system as claimed in claim 5, wherein said communicative means comprises a fluid passageway extending longitudinally through said catheter body from said branch of said catheter body to said balloon.

7. A vascular catheter system as claimed in claim 4, further comprising a reference mark placed on said operative catheter body at a longitudinal distance from said distal end of said operative catheter body, said longitudinal distance being slightly less than the length of said guiding catheter.

8. A method of removing a first over-the-wire operative catheter from a guiding catheter in a patient, and replacing it with a second operative catheter, over the same guidewire, the method comprising the steps of:

providing said first operative catheter with a rupturable membrane along one side of its guidewire channel, and an operative means mounted on a distal end of said operative catheter;

withdrawing said first operative catheter from said guiding catheter, while stripping said guidewire from said operative catheter by tearing said guidewire through said rupturable membrane from a proximal end of said operative catheter;

threading the proximal end of said guidewire through a distal end of a guidewire channel on a second operative catheter; and inserting said second operative catheter into said guiding catheter over said guidewire.

9. A method of removing a first over-the-wire operative catheter from a guiding catheter in a patient, and replacing it with a second operative catheter, over the same guidewire, as claimed in claim 8, further comprising the steps of:

bending said operative catheter to expose said rupturable membrane on the outside of the bend; and pushing said proximal end of said guidewire through said rupturable membrane at a selected location.

10. A method of rapid replacement of a first operative catheter with a second operative catheter, the method comprising the steps of:

providing a guiding catheter having a releasable seal;

inserting said guiding catheter through an internal passageway of a patient to a selected treatment area;

providing a first operative catheter having a guidewire channel and a rupturable membrane along a side of said guidewire channel;

providing a guidewire;

positioning said guidewire through said guidewire channel;

inserting said first operative catheter and said guidewire through said guiding catheter to a selected depth;

selectively sealingly engaging said releasable seal around said first operative catheter;

withdrawing said first operative catheter from said guiding catheter, while holding said guidewire in place by its proximal end, and while tearing said guidewire through said rupturable membrane from a proximal end of said operative catheter;

providing a second operative catheter having a guidewire channel and a rupturable membrane along a side of said guidewire channel;

threading said proximal end of said guidewire through said guidewire channel on said second operative catheter; and inserting said second operative catheter into said guiding catheter over said guidewire.

11. A method of rapid replacement of a first operative catheter with a second operative catheter, as claimed in claim 10, further comprising the steps of:

bending said second operative catheter to expose said rupturable membrane on the outside of the bend; and pushing said proximal end of said guidewire through said rupturable membrane at a selected location.

* * * * *